(12) United States Patent
Haga et al.

(10) Patent No.: US 11,166,938 B2
(45) Date of Patent: Nov. 9, 2021

(54) EXTERNAL COMPOSITION CONTAINING ASCORBIC ACID AND/OR SALTS THEREOF

(71) Applicant: ROHTO PHARMACEUTICAL CO., LTD., Osaka (JP)

(72) Inventors: Masatoshi Haga, Osaka (JP); Yuya Hayashi, Osaka (JP)

(73) Assignee: ROHTO PHARMACEUTICAL CO., LTD., Osaka (JP)

( * ) Notice: Subject to any disclaimer, the term of this patent is extended or adjusted under 35 U.S.C. 154(b) by 159 days.

(21) Appl. No.: 16/313,876

(22) PCT Filed: Jun. 28, 2017

(86) PCT No.: PCT/JP2017/023743
§ 371 (c)(1),
(2) Date: Dec. 27, 2018

(87) PCT Pub. No.: WO2018/003850
PCT Pub. Date: Jan. 4, 2018

(65) Prior Publication Data
US 2019/0151284 A1   May 23, 2019

(30) Foreign Application Priority Data

Jun. 28, 2016 (JP) .................................. 2016-127462
Feb. 28, 2017 (JP) ............................. JP2017-036355

(51) Int. Cl.
| | |
|---|---|
| *A61K 31/375* | (2006.01) |
| *A61K 8/86* | (2006.01) |
| *A61P 17/10* | (2006.01) |
| *A61P 17/18* | (2006.01) |
| *A61K 31/357* | (2006.01) |
| *A61P 17/00* | (2006.01) |
| *A61K 47/22* | (2006.01) |
| *A61K 8/34* | (2006.01) |
| *A61K 8/41* | (2006.01) |
| *A61K 8/55* | (2006.01) |
| *A61K 8/67* | (2006.01) |
| *A61K 9/00* | (2006.01) |
| *A61K 47/18* | (2017.01) |
| *A61K 47/24* | (2006.01) |
| *A61Q 19/02* | (2006.01) |
| *A61Q 19/08* | (2006.01) |
| *A61K 47/10* | (2017.01) |

(52) U.S. Cl.
CPC ............ *A61K 31/375* (2013.01); *A61K 8/345* (2013.01); *A61K 8/416* (2013.01); *A61K 8/553* (2013.01); *A61K 8/676* (2013.01); *A61K 8/86* (2013.01); *A61K 9/006* (2013.01); *A61K 31/357* (2013.01); *A61K 47/18* (2013.01); *A61K 47/22* (2013.01); *A61K 47/24* (2013.01); *A61P 17/00* (2018.01); *A61P 17/10* (2018.01); *A61P 17/18* (2018.01); *A61Q 19/02* (2013.01); *A61Q 19/08* (2013.01); *A61K 9/0014* (2013.01); *A61K 47/10* (2013.01); *A61K 2800/262* (2013.01); *A61K 2800/5922* (2013.01)

(58) Field of Classification Search
CPC .... A61K 31/375; A61K 31/357; A61K 47/22; A61K 8/345; A61K 8/416; A61K 8/553; A61K 8/676; A61K 9/006; A61K 47/18; A61K 47/24; A61K 8/86; A61K 9/0014; A61K 2800/262; A61K 2800/5922; A61K 47/10; A61P 17/00; A61P 17/10; A61P 17/18; A61Q 19/02; A61Q 19/08
See application file for complete search history.

(56) References Cited

U.S. PATENT DOCUMENTS

| | | | |
|---|---|---|---|
| 2003/0134264 A1* | 7/2003 | Maeda | A61K 8/492 435/4 |
| 2013/0078205 A1* | 3/2013 | Dayan | A61P 17/00 424/60 |
| 2014/0155633 A1 | 6/2014 | Chen et al. | |
| 2016/0136078 A1 | 5/2016 | Chen et al. | |
| 2016/0158134 A1 | 6/2016 | Disalvo | |

FOREIGN PATENT DOCUMENTS

| | | |
|---|---|---|
| CN | 1660081 A | 8/2005 |
| JP | 62-95134 A | 5/1987 |
| JP | 3-5426 A | 1/1991 |
| JP | 2002-348228 A | 12/2002 |
| JP | 2005-225865 A | 8/2005 |
| JP | 2008-195712 A | 8/2008 |
| JP | 2010-70492 A | 4/2010 |
| JP | 2011-178735 A | 9/2011 |
| JP | 2012-176903 A | 9/2012 |
| JP | 2013-095691 A | 5/2013 |
| JP | 2013-227264 A | 11/2013 |
| WO | WO-00/78283 A1 | 12/2000 |
| WO | WO 01/72264 A2 | 10/2001 |
| WO | WO-02/19972 A2 | 3/2002 |

OTHER PUBLICATIONS

Office Action with English Translation issued in Indonesian Patent Application No. P00201900122 dated Oct. 11, 2019, 4 pages.
International Search Report and Written Opinion (ISA/JP) for PCT/JP2017/023743, dated Oct. 3, 2017, 10 pages.
Office Action in JP 2017-563140, dated Feb. 5, 2018, 9 pages.

(Continued)

*Primary Examiner* — Sue X Liu
*Assistant Examiner* — Andriae M Holt
(74) *Attorney, Agent, or Firm* — Foley & Lardner LLP

(57) ABSTRACT

Provided is an external composition excellent in stability and impression from use. An external composition containing (A) at least one member selected from the group consisting of ascorbic acid and salts of ascorbic acid, (B) at least one member selected from the group consisting of 3-O-ethylascorbic acid, salts of 3-O-ethylascorbic acid, and hydroxylated lecithin, and (C) polyethylene glycol is prepared.

12 Claims, 1 Drawing Sheet

(56) References Cited

OTHER PUBLICATIONS

Decision to Grant a Patent in JP 2017-563140, dated Apr. 27, 2018, 5 pages.
International Preliminary Report on Patentability issued in PCT/JP2017/023743 dated Jan. 10, 2019, 8 pages.
First Office Action on Chinese Patent Application No. 201780040059.5 dated Jul. 5, 2021 (26 pages).

* cited by examiner

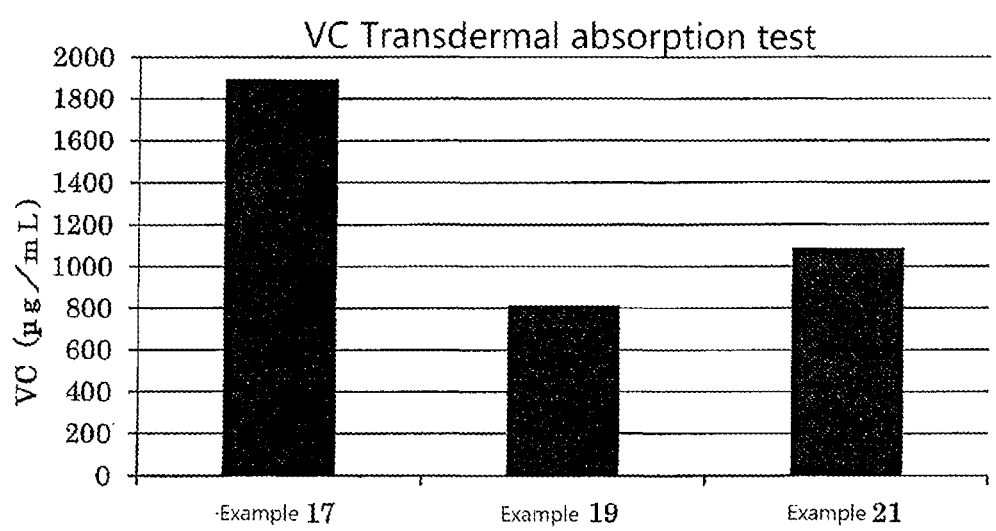

EXTERNAL COMPOSITION CONTAINING ASCORBIC ACID AND/OR SALTS THEREOF

CROSS-REFERENCE TO RELATED APPLICATIONS

This application is a national stage entry under 35 U.S.C. § 371 of International Patent Application No. PCT/JP2017/023743 filed Jun. 28, 2017, which claims priority to Japanese Patent Application Nos. 2016-127462 filed Jun. 28, 2016 and 2017-036355 filed Feb. 28, 2017, the entire content of each of which is hereby incorporated by reference.

TECHNICAL FIELD

The present invention relates to a composition for an external use containing (A) ascorbic acid and/or salts thereof.

BACKGROUND ART

It is known that ascorbic acid exhibits various effects such as anti-inflammatory effect, acne improvement effect, skin-whitening effect, anti-aging effect, antioxidant effect, cell activation effect by promoting synthesis of biological components such as collagen and the like, and effect of suppressing cytotoxicity or DNA damage of epidermal keratinocyte by ultraviolet light, and ascorbic acid is widely used as a skin external preparation in anticipation of these effects.

Since ascorbic acid is easily oxidized in the presence of water such as in an aqueous solution, it is required to reduce water in the preparation, but ascorbic acid cannot be sufficiently solubilized with a small amount of water.

Therefore, several methods for stably solubilizing ascorbic acid in aqueous skin external preparations have been investigated (for example, Patent Document 1: WO 02/19972 A, Patent Document 2: WO 00/78283 A, Patent Document 3: JP-A-2002-348228, Patent Document 4: JP-A-2005-225865).

PRIOR ART DOCUMENTS

Patent Documents

Patent Document 1: WO 02/19972 A
Patent Document 2: WO 00/78283 A
Patent Document 3: JP-A-2002-348228
Patent Document 4: JP-A-2005-225865

SUMMARY OF THE INVENTION

Problems to be Solved by the Invention

An object of the present invention is to provide an ascorbic acid-containing external composition having excellent stability.

Means for Solving the Problems

An external composition comprising ascorbic acid and/or salts thereof, in which various concentrations of ascorbic acid and/or salts thereof can be contained, is provided.

According to the investigations by the present inventors, it has been found that when ascorbic acid and/or salts thereof is blended in a high concentration, in some cases, they are not dissolved from the time of production, and even when they are dissolved at the time of production, they are precipitated in the case of, for example, being stored at a low temperature of 4° C. or the like.

As a result of extensive investigations to solve this problem, the present inventors have found that an external composition having excellent stability which can suppresses precipitation of ascorbic acid, and can suppress decomposition of ascorbic acid, by using (A) at least one member selected from the group consisting of ascorbic acid and salts of ascorbic acid, (B) at least one member selected from the group consisting of 3-O-ethylascorbic acid, salts of 3-O-ethylascorbic acid, and hydroxylated lecithin, and (C) polyethylene glycol, and have completed the present invention.

More specifically, the present invention provides the following external composition.

Item 1.
An external composition containing:
(A) at least one member selected from the group consisting of ascorbic acid and salts of ascorbic acid;
(B) at least one member selected from the group consisting of 3-O-ethylascorbic acid, salts of 3-O-ethylascorbic acid, and hydroxylated lecithin; and
(C) polyethylene glycol.

Item 2.
The external composition according to item 1, further containing (D) a low molecular weight betaine.

Item 3.
The external composition according to item 1 or 2, further containing (E) glycol ether.

Item 4.
The external composition according to any one of items 1 to 3, further containing (F) a polyhydric alcohol.

Item 5.
The external composition according to any one of items 1 to 4, wherein (B) is at least one member selected from the group consisting of 3-O-ethylascorbic acid and salts of 3-O-ethylascorbic acid, and hydroxylated lecithin.

Item 6.
The external composition according to any one of items 1 to 5, wherein a concentration of the ascorbic acid or a salt thereof is 3 w/w % to 40 w/w %.

Item 7.
The external composition according to any one of items 1 to 6, wherein the external composition is a solubilized external composition having a transmittance at a wavelength of 700 nm of 85 to 100%.

Item 8.
A method for imparting stability to an external composition containing (A) at least one member selected from the group consisting of ascorbic acid and salts of ascorbic acid, by a combined use of (A) at least one member selected from the group consisting of ascorbic acid and salts of ascorbic acid, (B) at least one member selected from the group consisting of 3-O-ethylascorbic acid, salts of 3-O-ethylascorbic acid, and hydroxylated lecithin, and (C) polyethylene glycol.

Item 9.
The method according to item 8, further combinedly using (D) a low molecular weight betaine.

Item 10.
The method according to item 8 or 9, further combinedly using (E) glycol ether.

Item 11.
The method according to any one of items 8 to 10, further combinedly using (F) a polyhydric alcohol.

Effect of the Invention

According to the present invention, it is possible to provide an external composition having excellent stability.

BRIEF DESCRIPTION OF THE DRAWINGS

FIG. 1 is a graph showing the results of a transdermal absorption test according to one embodiment of the external composition of the present invention.

MODE FOR CARRYING OUT THE INVENTION

The unit "w/w %" of the content herein is synonymous with "g/100 g".

The external composition of the present invention contains:
 (A) at least one member selected from the group consisting of ascorbic acid and salts of ascorbic acid;
 (B) at least one member selected from the group consisting of 3-O-ethylascorbic acid, salts of 3-O-ethylascorbic acid, and hydroxylated lecithin; and
 (C) polyethylene glycol.

One embodiment of the external composition of the present invention contains:
 (A) at least one member selected from the group consisting of ascorbic acid and salts of ascorbic acid;
 (B) at least one member selected from the group consisting of 3-O-ethylascorbic acid and salts of 3-O-ethylascorbic acid; and
 (C) polyethylene glycol.

Another embodiment of the external composition of the present invention contains:
 (A) at least one member selected from the group consisting of ascorbic acid and salts of ascorbic acid;
 (B) hydroxylated lecithin; and
 (C) polyethylene glycol.

Still another embodiment of the external composition of the present invention contains:
 (A) at least one member selected from the group consisting of ascorbic acid and salts of ascorbic acid;
 (B) at least one member selected from the group consisting of 3-O-ethylascorbic acid and salts of 3-O-ethylascorbic acid, and hydroxylated lecithin; and
 (C) polyethylene glycol.

The external composition of the present invention is stable in a wide concentration range of at least one member selected from the group consisting of (A) ascorbic acid and salts of ascorbic acid, and is highly safe.

[(A) At Least One Member Selected from the Group Consisting of Ascorbic Acid and Salts of Ascorbic Acid]

The ascorbic acid to be used in the present invention may be ascorbic acid that is commercially available as a component of a skin external preparation in the field of pharmaceuticals, quasi-drugs or cosmetics, which usually refers to L form ascorbic acid.

Salts of ascorbic acid can also be used. Here, the salt of ascorbic acid is a pharmaceutically acceptable salt. Examples of the salt of ascorbic acid include salts with an organic base (for example, salts with a tertiary amine such as trimethylamine salts, triethylamine salts, monoethanolamine salts, triethanolamine salts and pyridine salts, basic ammonium salts such as arginine, and the like), salts with an inorganic base (for example, alkali metal salts such as ammonium salts, sodium salts and potassium salts, alkaline earth metal salts such as calcium salts and magnesium salts, aluminum salts, and the like) and the like, but are not limited thereto. Particularly preferred salts of ascorbic acid are sodium salts and potassium salts. Specific examples thereof include sodium ascorbate, sodium ascorbyl monophosphate, sodium ascorbyl diphosphate, sodium ascorbyl triphosphate, sodium ascorbyl-2-sulfate, and the like.

In the present invention, ascorbic acid or a salt thereof can be used alone or in combination of two or more.

In the external composition of the present invention, the total content of the component (A) based on the total amount of the external composition is appropriately set depending on the balance with other components. The total content of the component (A) is preferably 0.1 w/w % or more, more preferably 1 w/w % or more, further preferably 2 w/w % or more, still more preferably 3 w/w % or more, and most preferably 10 w/w % or more, based on the total amount of the external composition. The total content of the component (A) is preferably 50 w/w % or less, more preferably 40 w/w % or less, further preferably 35 w/w % or less, and still more preferably 30 w/w % or less, based on the total amount of the external composition. The total content of the component (A) is preferably 0.1 w/w % to 50 w/w %, more preferably 1 w/w % to 40 w/w %, further preferably, 3 w/w % to 40 w/w %, still more preferably 3 w/w % to 30 w/w %, and most preferably 10 w/w % to 30 w/w %, based on the total amount of the external composition.

[(B) At Least One Member Selected from Group Consisting of 3-O-Ethylascorbic Acid, Salts of 3-O-Ethylascorbic Acid and Hydroxylated Lecithin]

(B-1) 3-O-Ethylascorbic acid or salt of 3-O-ethylascorbic Acid (Sometimes Referred to as B-1 Component in the Present Specification)

As 3-O-ethylascorbic acid to be used in the present invention, L-3-O-ethylascorbic acid is preferably used but it is not limited thereto.

3-O-Ethylascorbic acid can be synthesized by ethoxylating a hydroxyl group at the 3-position of ascorbic acid (for example, according to a known method described in JP-A-8-134055 or the like). As 3-O-ethylascorbic acid, a commercially available product can be used as it is. Examples of commercially available products include, in addition to "VC ethyl" manufactured by NIPPON FINE CHEMICAL CO., LTD., products manufactured by JUNSEI CHEMICAL CO., LTD., and the like, but are not limited thereto.

3-O-Ethylascorbic acid contributes to stability of the external composition of the present invention.

3-O-Ethylascorbic acid can also be used as a salt. Here, the salt of 3-O-ethylascorbic acid is a pharmaceutically acceptable salt. Examples of the salt of ascorbic acid include salts with an organic base (for example, salts with a tertiary amine such as trimethylamine salts, triethylamine salts, monoethanolamine salts, triethanolamine salts and pyridine salts, basic ammonium salts such as arginine, and the like), salts with an inorganic base (for example, alkali metal salts such as ammonium salts, sodium salts and potassium salts, alkaline earth metal salts such as calcium salts and magnesium salts, aluminum salts, and the like) and the like, but are not limited thereto. Particularly preferred salts of 3-O-ethylascorbic acid are sodium salts and potassium salts.

In the present invention, 3-O-ethylascorbic acid or a salt thereof can be used alone or in combination of two or more.

In the external composition of the present invention, the total content of the component (B-1) based on the total amount of the external composition is appropriately set depending on the balance with other components. The total content of the component (B-1) is preferably 0.005 w/w % or more, more preferably 0.01 w/w % or more, further preferably 0.02 w/w % or more, more preferably 0.05 w/w % or more, and most preferably 0.1 w/w % or more, based on the total amount of the external composition. Also, the total content of the component (B) is preferably 10 w/w % or less, more preferably 5 w/w % or less, further preferably 3 w/w % or less, more preferably 2 w/w % or less, and most preferably 1 w/w % or less, based on the total amount of the external composition. The total content of the component (B) is preferably 0.005 w/w % to 10 w/w %, more preferably 0.01 w/w % to 5 w/w %, further preferably 0.02 w/w % to 3 w/w %, and most preferably 0.1 w/w % to 2 w/w %, based on the total amount of the external composition.

In the external composition of the present invention, the ratio of the amount of the component (B-1) to the component (A) is such that the total content of the component (B-1) is preferably 0.0001 to 100 parts by weight, more preferably 0.001 to 100 parts by weight, further preferably 0.005 to 10 parts by weight, and most preferably 0.005 to 1 part by weight, based on 1 part by weight of the total content of the component (A).

(B-2) Hydroxylated Lecithin (Sometimes Referred to as B-2 Component in the Present Specification)

The hydroxylated lecithin used in the present invention is one obtained by introducing a hydroxyl group into an unsaturated carbon chain in lecithin. Lecithin can be extracted from plants or animals. The origin of hydroxylated lecithin used in the present invention is not particularly limited, and examples thereof include hydroxylated soybean lecithin (hydroxylated soybean phospholipid), hydroxylated egg yolk lecithin (hydroxylated egg yolk phospholipid), and the like. Hydroxylated lecithin containing phosphatidylcholine, phosphatidylethanolamine, phosphatidylinositol and/or the like as a component is preferably used, but it is not limited thereto. From the viewpoint of the effect of the present invention, hydroxylated soybean lecithin is preferably used. As hydroxylated soybean lecithin, LECINOL SH-50 or LECINOL WS-50 manufactured by Nikko Chemicals Co., Ltd. can be obtained and used. Both LECINOL SH-50 and LECINOL WS-50 consist of 50% by weight of hydroxylated lecithin and 50% by weight of glycerin.

In the external composition of the present invention, the total content of the component (B-2) based on the total amount of the external composition is appropriately set depending on the balance with other components. The total content of the component (B-2) is preferably 0.005 w/w % or more, more preferably 0.01 w/w % or more, further preferably 0.02 w/w % or more, still more preferably 0.05 w/w % or more, and most preferably 0.1 w/w % or more, based on the total amount of the external composition. Also, the total content of the component (B-2) is preferably 10 w/w % or less, more preferably 5 w/w % or less, further preferably 3 w/w % or less, still more preferably 2 w/w % or less, and most preferably 1 w/w % or less, based on the total amount of the external composition. The total content of the component (B-2) is preferably 0.005 w/w % to 10 w/w %, more preferably 0.01 w/w % to 5 w/w %, further preferably 0.02 w/w % to 3 w/w %, and most preferably 0.1 w/w % to 1 w/w %, based on the total amount of the external composition.

In the external composition of the present invention, the ratio of the content of the component (B-2) to the component (A) is such that the total content of the component (B-2) is preferably 0.0001 to 1000 parts by weight, more preferably 0.001 to 100 parts by weight, further preferably 0.005 to 10 parts by weight, still preferably 0.05 to 1 parts by weight, and most preferably 0.01 to 0.5 parts by weight, based on 1 part by weight of the total content of the component (A).

[(C) Polyethylene Glycol]

The polyethylene glycol used in the present invention preferably has a degree of polymerization of 4 or more, and is used in pharmaceuticals, quasi-drugs, or cosmetics, as a base or the like. In the present invention, relatively low molecular weight polyethylene glycol is preferably used. Specifically, polyethylene glycol with an average molecular weight of about 150 to 1000 is preferable, and polyethylene glycol of about 170 to 800 is more preferable, while it is not limited thereto. Specific examples of such polyethylene glycol include polyethylene glycol 200, polyethylene glycol 300, polyethylene glycol 400, polyethylene glycol 500, polyethylene glycol 600, polyethylene glycol 700, polyethylene glycol 800, and the like. Since there are commercially available products for these polyethylene glycols, those commercially available products can also be obtained and used. Specific examples of the commercially available products include polyethylene glycol 200, polyethylene glycol 300, polyethylene glycol 400 and polyethylene glycol 600 sold by NOF CORPORATION, polyethylene glycol 200, polyethylene glycol 300, polyethylene glycol 400 and polyethylene glycol 600 of Sanyo Chemical Industries, Ltd., and the like.

Here, the average molecular weight can be obtained, for example, according to the average molecular weight test described in the section of polyethylene glycol on quasi-drug raw material specification 2006.

[Measurement Method of Average Molecular Weight of Polyethylene Glycol with Average Molecular Weight of 190 to 210]

About 0.8 g of polyethylene glycol is precisely weighed and placed in a pressure-resistant stoppered bottle of about 200 mL, about 25 mL of pyridine is added thereto, and the mixture is warmed to melt and allowed to cool. Separately, 42 g of phthalic anhydride is taken and added to a 1-L shielded ground-in stopper bottle to which accurately weighed 300 mL of freshly distilled pyridine is added, and dissolved by shaking it strongly, then left for over 16 hours. 25 mL of this solution is accurately weighed, and added to the above pressure-resistant ground-in stopper bottle, and this bottle is tightly wrapped with a strong cloth and placed in a water bath previously heated to 98° C.±2° C. At this time, the liquid in the bottle is soaked in the liquid of the water bath. The liquid is heated at 98° C.±2° C. for 30 minutes, and then allowed to cool to room temperature. Next, 50 mL of a 0.5 mol/L sodium hydroxide solution is accurately added, and this solution is titrated with a 0.5 mol/L sodium hydroxide solution. At this time, 5 drops of phenolphthalein·pyridine solution (1→100) are used as an indicator. However, the end point of the titration shall be a time when the liquid exhibits a pale red color which persists for 15 seconds. A blank test is performed in the same manner.

The obtained value is applied to the following formula to calculate the average molecular weight.

$$\text{Average molecular weight} = [\text{Amount of sample (g)} \times 4000]/(a-b)$$

a: Consumption amount (mL) of 0.5 mol/L sodium hydroxide solution in the blank test b: Consumption amount (mL) of 0.5 mol/L sodium hydroxide solution in the test of the sample Even in the case of polyethylene glycol with an average molecular weight other than 190 to 210, while the weighed amount is different, the other is in accordance with the test method of polyethylene glycol with an average molecular weight of 190 to 210.

These polyethylene glycols can be used alone or in combination of two or more kinds.

By using polyethylene glycol, the external composition of the present invention can be made into a composition having excellent stability.

In the external composition of the present invention, the total content of the component (C) based on the total amount of the external composition is preferably 0.01 w/w % or more, more preferably 0.1 w/w % or more, further preferably 0.5 w/w % or more, still more preferably 1 w/w % or more, and most preferably 5 w/w % or more. The total content of the component (C) is preferably 90 w/w % or less, more preferably 80 w/w % or less, further preferably 70 w/w % or less, still more preferably 65 w/w % or less, and most preferably 60 w/w % or less, based on the total amount of the external composition. The total content of the component (C) is preferably 0.01 w/w % to 90 w/w %, more preferably 0.1 w/w % to 80 w/w %, further preferably, 0.5 w/w % to 70 w/w %, still more preferably 0.5 w/w % to 60 w/w %, and most preferably 1 w/w % to 60 w/w %, based on the total amount of the external composition.

In the external composition of the present invention, the ratio of the amount of the component (C) to the component (A) is such that the total content of the component (C) is preferably 0.001 to 100 parts by weight, more preferably 0.01 to 100 parts by weight, further preferably 0.01 to 50 parts by weight, still preferably 0.01 to 20 parts by weight, and most preferably 0.01 to 10 parts by weight, based on 1 part by weight of the total content of the component (A).

By containing the components (A), (B), and (C), the external composition of the present invention becomes an external composition having good stability.

In addition to the components (A), (B) and (C), the external composition of the present invention may contain (D) low molecular weight betaine and/or (E) glycol ether and/or (F) a polyhydric alcohol as far as it does not impair the effect of the present invention.

[(D) Low Molecular Weight Betaine]

In the present invention, the low molecular weight betaine refers to one which forms an amphoteric ion in a molecule with a molecular weight of 200 or less. Specific examples thereof include a quaternary ammonium base, a quaternary phosphonium base, a tertiary sulfonium base and the like, and these show little property as a surfactant. Among them, preferable examples include N,N,N-trialkylamino acids represented by the following chemical formula

[Chemical formula 1]

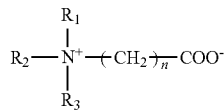

wherein $R_1$, $R_2$ and $R_3$ each independently represent an alkyl group having 1 to 6 carbon atoms, and n represents 1 to 6.

As $R_1$ to $R_3$, a linear or branched alkyl group having 1 to 6 carbon atoms can be widely used. That is, examples thereof include a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group, an isohexyl group, a 3-methylpentyl group, a 2,2-dimethylbutyl group, a 2,3-dimethylbutyl group, and the like. $R_1$ to $R_3$ may be the same or different.

Specific examples of the low molecular weight betaine include, in the case of n=1, trimethylglycine, triethylglycine, tripropylglycine and triisopropylglycine; in the case of n=2, trimethyl-β-alanine; in the case of n=3, trimethyl-γ-aminobutyric acid; and the like, and preferred is trimethylglycine.

In addition, these low molecular weight betaines may be substituted, specific examples include, in the case of n=1, N,N,N-trimethylalanine, N,N,N-triethylalanine, N,N,N-triisopropylalanine and N,N,N-trimethylmethylalanine, carnitine, acetylcarnitine and the like, and preferred is carnitine.

Further, these also can be synthesized, and commercially available products can be used as they are.

These low molecular weight betaines can be used alone or in combination of two or more kinds.

The low molecular weight betaine may contribute to higher stability of the external composition of the present invention.

In the external composition of the present invention, the total content of the component (D) based on the total amount of the external composition is preferably 0.01 w/w % or more, more preferably 0.1 w/w % or more, further preferably 0.5 w/w % or more, still more preferably 1 w/w % or more, and most preferably 2 w/w % or more. The total content of the component (D) is preferably 30 w/w % or less, more preferably 25 w/w % or less, further preferably 20 w/w % or less, still more preferably 15 w/w % or less, and most preferably 10 w/w % or less, based on the total amount of the external composition. The content of the component (D) is preferably 0.01 w/w % to 30 w/w %, more preferably 0.1 w/w % to 25 w/w %, further preferably, 0.5 w/w % to 20 w/w %, still more preferably 1 w/w % to 15 w/w %, and most preferably 2 w/w % to 10 w/w %, based on the total amount of the external composition.

In the external composition of the present invention, the ratio of the amount of the component (D) to the component (A) is preferably 0.0001 to 100 parts by weight, more preferably 0.001 to 100 parts by weight, further preferably 0.01 to 10 parts by weight, still preferably 0.025 to 5 parts by weight, and most preferably 0.025 to 1 parts by weight, based on 1 part by weight of the total content of the component (A).

[(E) Glycol Ether]

The glycol ether used in the present invention is not particularly limited as long as it is used as a component of a skin external preparation in the field of pharmaceuticals, quasi-drugs or cosmetics. Glycol ether may be used as long as it dissolves 10 g or more in 100 g of water. Glycol ether with a degree of polymerization of 2 or less is preferred. Specific examples thereof include diethylene glycol monomethyl ether, diethylene glycol monoethyl ether, diethylene glycol monopropyl ether, diethylene glycol monobutyl ether, diethylene glycol monoisobutyl ether, diethylene glycol dimethyl ether, ethylene glycol monobutyl ether, ethylene glycol monomethyl ether, ethylene glycol monoethyl ether, triethylene glycol monobutyl ether, tetraethylene glycol monobutyl ether, propylene glycol monomethyl ether, propylene glycol monoethyl ether, propylene glycol monopropyl ether, dipropylene glycol monomethyl ether, dipropylene glycol monoethyl ether, dipropylene glycol monopropyl ether, and the like. Preferred are diethylene glycol monomethyl ether, diethylene glycol monoethyl ether, diethylene glycol monopropyl ether, diethylene glycol monobutyl ether, diethylene glycol monoisobutyl ether, diethylene glycol dimethyl ether, ethylene glycol monobutyl ether, ethylene glycol monomethyl ether, ethylene glycol monoethyl ether, triethylene glycol monobutyl ether, tetraethylene glycol monobutyl ether, propylene glycol monomethyl ether, propylene glycol monoethyl ether, propylene glycol monopropyl ether, dipropylene glycol monomethyl ether, dipropylene glycol monoethyl ether, and dipropylene glycol monopropyl ether. More preferred are diethylene glycol monomethyl ether, diethylene glycol monoethyl ether, diethylene glycol monopropyl ether, ethylene glycol monobutyl ether, triethylene glycol monobutyl ether, tetraethylene glycol monobutyl ether, propylene glycol monomethyl ether, propylene glycol monoethyl ether, propylene glycol monopropyl ether, dipropylene glycol monomethyl ether, dipropylene glycol monoethyl ether, and dipropylene glycol monopropyl ether. Among them, it is particularly preferable to appropriately contain diethylene glycol monoethyl ether.

These glycol ethers can be used alone or in combination of two or more kinds.

Glycol ethers, for example, can contribute to better skin permeability of the external composition of the present invention.

In the external composition of the present invention, the total content of the component (E) based on the total amount of the external composition is preferably 0.1 w/w % or more, more preferably 1 w/w % or more, further preferably 2 w/w % or more, still more preferably 5 w/w % or more, and most preferably 10 w/w % or more. The total content of the component (E) is preferably 80 w/w % or less, more preferably 75 w/w % or less, further preferably 70 w/w % or less, still more preferably 60 w/w % or less, and most preferably 55 w/w % or less, based on the total amount of the external composition. The total content of the component (E) is preferably 0.1 w/w % to 80 w/w %, more preferably 1 w/w % to 75 w/w %, further preferably 5 w/w % to 70 w/w %, and most preferably 10 w/w % to 55 w/w %, based on the total amount of the external composition.

In the external composition of the present invention, the ratio of the amount of the component (E) to the component (A) is preferably 0.0001 to 100 parts by weight, more preferably 0.001 to 100 parts by weight, further preferably 0.01 to 50 parts by weight, still preferably 0.05 to 10 parts by weight, and most preferably 0.1 to 5 parts by weight, based on 1 part by weight of the total content of the component (A).

[(F) Polyhydric Alcohol]

The polyhydric alcohol used in the present invention is not particularly limited as long as it is used as a component of a skin external preparation in the field of pharmaceuticals, quasi-drugs or cosmetics. The polyhydric alcohol may be added for moisturizing or as a solubilizing agent, while it is not limited. Specific examples thereof include glycerin, diglycerin, dipropylene glycol, 1,3-propanediol, 1,3-butylene glycol, 1,2-propanediol, and the like. Preferred are diglycerin, dipropylene glycol, and 1,3-propanediol. Among them, it is particularly preferable to appropriately contain dipropylene glycol and 1,3-propanediol.

In the external composition of the present invention, the total content of the component (F) based on the total amount of the external composition is preferably 0.1 to 25 w/w % or more, more preferably 0.5 to 20 w/w % or more, and still more preferably 0.5 to 10 w/w % or more.

In the external composition of the present invention, the ratio of the amount of the component (F) to the component (A) is preferably 0.0001 to 300 parts by weight, more preferably 0.001 to 300 parts by weight, further preferably 0.01 to 10 parts by weight, still preferably 0.05 to 10 parts by weight, and most preferably 0.05 to 3 parts by weight, based on 1 part by weight of the total content of the component (A).

[Other Components]

In addition to the above components (A), (B) and (C), the external composition of the present invention may further contain, for the purpose of enhancing or supplementing various actions of ascorbic acid or for adding another effective actions, various components such as skin-whitening components, anti-inflammatory components, antibacterial components, cell-activating components, astringent components, antioxidant components, acne improving components, anti-aging components, biological component synthesis promoting components such as collagen, blood circulation promoting components, moisturizing components and anti-aging components alone or in combination of two or more. Preferably, it is one or more components of skin-whitening components, anti-inflammatory components, antibacterial components, cell-activating components, astringent components, antioxidant components, anti-aging components or moisturizing components. Examples of particularly preferable combinations of these components include a combination with a skin-whitening component, a combination of a skin-whitening component and an antioxidant component, each combination with an antioxidant component, a combination with an anti-aging component, and each combination of a skin-whitening component and an anti-aging component. These components are not particularly limited as long as they are conventionally used as components of skin external preparations in the field of pharmaceuticals, quasi-drugs, or cosmetics, and are used in the future, and arbitrary ones can be appropriately selected and used.

Here, examples of skin-whitening components include arbutin; ellagic acid; phytic acid; rucinol; camomilla ET; vitamin A or derivatives thereof, vitamin E or its derivative, vitamins such as pantothenic acid or derivatives thereof, hydroquinone, tranexamic acid, Kojic acid, and the like. Among them, preferable examples include pantothenic acid or derivatives thereof, ellagic acid, phytic acid, vitamin A or derivatives thereof, and vitamin E or derivatives thereof. One or more of these skin-whitening components may be used.

Plant components having skin-whitening effect may be used as skin-whitening components. Examples of such plant components include components derived from plants such as iris, almond, aloe, ginkgo, oolong tea, rose fruit, scutellaria root, Coptis Rhizome, St. John's wort (Hypericum erectum Thunb), dead nettle, seaweed, pueraria root, gardenia, Sophorae Radix, chlorella, gallnut, wheat, rice, rice germ, orizanol, rice bran, Asiasari Radix, zanthoxylum fruit, perilla, peony root, Cnidium Rhizome, mulberry bark, soybeans, fermented soybeans, tea, Japanese angelica, Calendula officinalis, garlic, hamamelis, safflower, moutan bark, coix seeds, Angelica acutiloba Kitagawa, amethyst, gambir, Japanese andromeda, bracken, Podocarpus macrophyllus, Celtis sinensis, persimmon (Diospyros kaki), catalpa, black soybeans, gentian, figwort (Scrophularia ningpoensis), sarsaparilla, French beans, cimicifuga rhizome, Paris polyphylla Smith, sage, Peucedani Radix, Japanese radish, azalea, Lespedeza homoloba, seeds of Cuscuta chinensis Lam., Picrasma quassioides, parsley, hollies, hops, Lespedeza cyrtobotrya, cloves, and licorice. Preferable examples are plant-derived components of iris, aloe, ginkgo, oolong tea, rose fruit, scutellaria root, Coptis Rhizome, St. John's wort (Hypericum erectum Thunb), dead nettle, seaweed, pueraria root, gardenia, Sophorae Radix, gallnut, wheat, rice, rice bran, Asiasari Radix, zanthoxylum fruit, perilla, peony, Cnidium Rhizome, mulberry bark, tea, Japanese angelica, Calendula officinalis, hamamelis, safflower, moutan bark, coix seeds, amethyst, gambir, Celtis sinensis, persimmon (Diospyros kaki), catalpa, black soybeans, gentian, sarsaparilla, French beans, Paris polyphylla Smith, sage, Peucedani Radix, Japanese radish, azalea, Lespedeza homoloba, seeds of Cuscuta chinensis Lam., Picrasma quassioides, parsley, hollies, hops, cloves, licorice and Japanese angelica. More preferable examples are plant-derived components of iris, aloe, ginkgo, rose fruit, scutellaria root, Coptis Rhizome, St. John's wort (Hypericum erectum Thunb), gardenia, Sophorae Radix, rice, rice bran, Asiasari Radix, peony, Cnidium Rhizome, mulberry bark, tea, Japanese angelica, Calendula officinalis, hamamelis, safflower, moutan bark, amethyst, gambir, Celtis sinensis, persimmon (Diospyros kaki), sage, Japanese radish, azalea, parsley, hops, licorice and coix seeds.

When using these plant components in the external composition of the present invention, the form of the plant component is not particularly limited, and these can be usually used in the mode of a plant essence (plant extract), essential oil, or the like. Incidentally, the inside of parenthesis in the above plant components is the kind of plant, alias or crude drug name.

In the case of using the skin-whitening component, the ratio in the external composition of the present invention is preferably 0.0003 to 10 w/w %, and more preferably 0.01 to 5 w/w %. Also, it is desirable to blend a skin-whitening component in a ratio of 0.00001 to 10 parts by weight, preferably 0.00005 to 5 parts by weight, and more preferably 0.0001 to 1 part by weight, based on 1 part by weight of the total content of the component (A) contained in the external composition of the present invention.

In the case of using a plant component having skin-whitening effect as a skin-whitening component, it can be used alone or in combination of two or more kinds depending on the purpose. In the case of using the plant component as a skin-whitening component, the ratio in the external composition of the present invention is usually 0.00001 to 20 w/w %, preferably 0.0001 to 15 w/w %, and more preferably 0.001 to 10 w/w %, in terms of extract such as essence and essential oil. Also, it is desirable to blend a plant component in a ratio of 0.000001 to 1 part by weight, and preferably 0.00001 to 0.5 parts by weight, based on 1 part by weight of the total content of the component (A).

Examples of anti-inflammatory components include allantoin, calamine, glycyrrhizic acid or derivatives thereof, glycyrrhetic acid or derivatives thereof, zinc oxide, guaiazulene, tocopherol acetate, pyridoxine hydrochloride, menthol, camphor, turpentine oil, indomethacin, salicylic acid or derivatives thereof, and the like. Preferred are allantoin, glycyrrhizic acid or derivatives thereof, glycyrrhetic acid or derivatives thereof, guaiazulene, and menthol.

In the case of using the anti-inflammatory component, the ratio in the external composition of the present invention is preferably 0.0003 to 10 w/w %, and more preferably 0.01 to 5 w/w %. Also, it is desirable to blend an anti-inflammatory component in a ratio of 0.00001 to 10 parts by weight, preferably 0.00005 to 5 parts by weight, and more preferably 0.0001 to 1 part by weight, based on 1 part by weight of the total content of the component (A) contained in the external composition of the present invention.

Examples of antibacterial components include chlorhexidine, salicylic acid, benzalkonium chloride, acrinol, ethanol, benzethonium chloride, cresol, gluconic acid and derivatives thereof, povidone-iodine, potassium iodide, iodine, isopropyl methylphenol, triclocarban, triclosan, Photosensitizing Dye No. 101, Photosensitizing Dye No. 201, parabens, phenoxyethanol, 1,2-pentanediol, alkyldiaminoglycine hydrochloride, and the like. Preferable examples include benzalkonium chloride, benzethonium chloride, gluconic acid and derivatives thereof, isopropyl methylphenol, triclocarban, triclosan, Photosensitizing Dye No. 101, Photosensitizing Dye No. 201, parabens, phenoxyethanol, 1,2-pentanediol, alkyldiaminoglycine hydrochloride, and the like. More preferred are benzalkonium chloride, gluconic acid and derivatives thereof, benzethonium chloride, and isopropyl methylphenol.

In the case of using the antibacterial component, the ratio in the external composition of the present invention is preferably 0.0003 to 10 w/w %, and more preferably 0.01 to 5 w/w %. Also, it is desirable to blend an antibacterial component in a ratio of 0.00001 to 10 parts by weight, preferably 0.00005 to 5 parts by weight, and more preferably 0.0001 to 1 part by weight, based on 1 part by weight of the total content of the component (A) contained in the external composition of the present invention.

Examples of cell-activating components include amino acids such as γ-aminobutyric acid and ϑ-aminocaproic acid; vitamins such as retinol, thiamine, riboflavin, pyridoxine hydrochloride and pantothenic acid; α-hydroxy acids such as glycolic acid and lactic acid; tannins, flavonoids, saponins, allantoin, Photosensitizing Dye No. 301, and the like. Preferred are amino acids such as γ-aminobutyric acid and ϑ-aminocaproic acid; and vitamins such as retinol, thiamine, riboflavin, pyridoxine hydrochloride, and pantothenic acid.

In the case of using the cell-activating component, the ratio in the external composition of the present invention is preferably 0.0003 to 10 w/w %, and more preferably 0.01 to 5 w/w %. Also, it is desirable to blend a cell-activating component in a ratio of 0.00001 to 10 parts by weight, preferably 0.00005 to 5 parts by weight, and more preferably 0.0001 to 1 part by weight, based on 1 part by weight of the total content of the component (A) contained in the external composition of the present invention.

Examples of astringent components include metal salts such as alum, chlorohydroxyaluminum, aluminum chloride, aluminum salt of allantoin, zinc sulfate and aluminum potassium sulfate; and organic acids such as tannic acid, citric acid, lactic acid and succinic acid. Preferred are alum, chlorohydroxyaluminum, aluminum chloride, aluminum salt of allantoin, aluminum potassium sulfate, and tannic acid.

In the case of using an astringent component, the ratio in the external composition of the present invention is usually 0.0003 to 10 w/w %, and preferably 0.01 to 5 w/w %. Also, it is desirable to blend an astringent component in a ratio of 0.00001 to 10 parts by weight, preferably 0.00005 to 5 parts by weight, and more preferably 0.0001 to 1 part by weight, based on 1 part by weight of the total content of the component (A) contained in the external composition of the present invention.

Examples of the antioxidant component include tocopherols and derivatives thereof, butylhydroxyanisole, dibutylhydroxytoluene, sodium bisulfite, erythorbic acid and salts thereof, flavonoids, glutathione, glutathione peroxidase, glutathione-S-transferase, catalase, superoxide dismutase, thioredoxin, taurine, thiotaurine, hypotaurine, and the like. Preferred are tocopherols and derivatives thereof, thiotaurine, hypotaurine, thioredoxin, and flavonoids.

In the case of using an antioxidant component, the ratio in the external composition of the present invention is usually 0.00001 to 10 w/w %, preferably 0.0001 to 5 w/w %, and more preferably 0.001 to 5 w/w %. Also, it is desirable to blend an antioxidant component in a ratio of preferably 0.00001 to 10 parts by weight, preferably 0.00005 to 5 parts by weight, and more preferably 0.0001 to 1 part by weight, based on 1 part by weight of the total content of the component (A) contained in the external composition of the present invention.

Examples of anti-aging components include retinoids (retinol, retinoic acid, retinal, and the like), pangamic acid, kinetin, ursolic acid, turmeric extracts, sphingosine derivatives, silicon, silicic acid, N-methyl-L-serine, mevalonolactone, and the like. Preferred are retinoids (retinol, retinoic acid, retinal, and the like) and kinetin.

In the case of using the anti-aging components, the ratio in the external composition of the present invention is preferably 0.0003 to 10 w/w %, and more preferably 0.01 to 5 w/w %. Also, it is desirable to blend an anti-aging component in a ratio of 0.00001 to 10 parts by weight, preferably 0.00005 to 5 parts by weight, and more preferably 0.0001 to 1 part by weight, based on 1 part by weight of the total content of the component (A) contained in the external composition of the present invention.

Examples of moisturizing components include amino acids such as alanine, serine, leucine, isoleucine, threonine, glycine, proline, hydroxyproline, glucosamine and theanine, and derivatives thereof; peptides such as collagen, collagen peptide and gelatin; sugar alcohols such as sorbitol; phospholipids such as lecithin and hydrogenated lecithin; mucopolysaccharides such as hyaluronic acid, heparin and chondroitin; NMF-derived components such as lactic acid, sodium pyrrolidone carboxylate and urea, plant extracts such as pennywort, artichoke, grapefruit, bilberry, rosemary and glasswort, yeast extracts, polyglutamic acid, and the like. Preferred are alanine, serine, glycine, proline, hydroxyproline, glucosamine, theanine, collagen, collagen peptide, hydrogenated lecithin, hyaluronic acid, heparin, chondroitin, lactic acid, sodium pyrrolidone carboxylate, plant extracts such as pennywort, artichoke, grapefruit, bilberry, rosemary and glasswort, and polyglutamic acid. Among them, it is particularly preferable to appropriately contain extract of pennywort, artichoke or grapefruit.

In the case of using a moisturizing component, the ratio in the external composition of the present invention is usually 0.00001 to 10 w/w %, preferably 0.00001 to 5 w/w %, and more preferably 0.0001 to 5 w/w %. Also, it is desirable to blend a moisturizing component in a ratio of preferably added in an amount of 0.000001 to 1 part by weight, and preferably 0.00001 to 0.5 parts by weight, based on 1 part by weight of the total content of the component (A) contained in the external composition of the present invention.

In addition to the above components, a surfactant, a solubilizing component, a fat or oil, a saccharide or a transdermal absorption promoting component can be further blended to the external composition of the present invention. In particular, by mixing a surfactant, a solubilizing component or a fat or oil, it is possible to further improve stability of ascorbic acid in an aqueous solvent, effectiveness, and impression from use.

Examples of the surfactant used herein include various nonionic surfactants such as POE-branched alkyl ethers such as polyoxyethylene (hereinafter referred to as POE)-octyldodecyl alcohol and POE-2-decyltetradecyl alcohol; POE-alkyl ethers such as POE-oleyl alcohol ether and POE-cetyl alcohol ether; sorbitan esters such as sorbitan monooleate, sorbitan monoisostearate and sorbitan monolaurate; POE-sorbitan esters such as POE-sorbitan monooleate, POE-sorbitan monoisostearate and POE-sorbitan monolaurate; glycerin fatty acid esters such as glycerin monooleate, glycerin monostearate and glycerin monomyristate; POE-glycerin fatty acid esters such as POE-glycerin monooleate, POE-glycerin monostearate and POE-glycerin monomyristate; POE-hydrogenated castor oil fatty acid esters such as POE-dihydrocholesterol ester, POE-hydrogenated castor oil and POE-hydrogenated castor oil isostearate; POE-alkylaryl ethers such as POE-octylphenyl ether; glycerin alkyl ethers such as monoisostearyl glyceryl ether and monomyristyl glyceryl ether; and POE-glycerin alkyl ethers such as POE-monostearyl glyceryl ether and POE-monomyristyl glyceryl ether; polyglycerol fatty acid ester such as diglyceryl monostearate, decaglyceryl decastearate, decaglyceryl decaisostearate and diglyceryl diisostearate; naturally occurring surfactants such as lecithin, hydrogenated lecithin, saponin, surfactin sodium, cholesterol and bile acids, and the like. These surfactants may be used singly or in any combination of two or more.

When a surfactant is used, the ratio in the external composition of the present invention is not particularly limited as far as it does not affect the skin and mucous membranes and does not impair the effect of the present invention, and it can be appropriately selected and used in a range such that it is contained in a ratio of 0.01 to 30 w/w % in the external composition of the present invention. From the viewpoint of stability of the active ingredient in the external composition of the present invention, impression from use on the skin and the like, the ratio of the surfactant is in a range of preferably 0.1 to 20 w/w %, and more preferably 0.5 to 10 w/w %. Also, the ratio of the surfactant based on 1 part by weight of the total content of the component (A) contained in the external composition of the present invention is in a range of 0.0001 to 1 part by weight, preferably 0.0001 to 0.5 parts by weight, and more preferably 0.001 to 0.4 parts by weight. Furthermore, from the viewpoint of stably solubilizing ascorbic acid in the external composition of the present invention, for example, the ratio of the surfactant based on 1 part by weight of the total content of component (A) is in a range of preferably 0.001 to 0.1 parts by weight, more preferably 0.001 to 0.05 parts by weight, and still more preferably 0.001 to 0.04 parts by weight.

The fats and oils are not particularly limited as long as they are used as components of external preparations in the field of pharmaceuticals, quasi-drugs or cosmetics. Examples thereof include synthetic fats and oils such as medium-chain fatty acid triglycerides; vegetable fats and oils such as soybean oil, rice oil, rapeseed oil, cottonseed oil, sesame oil, safflower oil, castor oil, olive oil, cacao oil, camellia oil, sunflower oil, palm oil, linseed oil, perilla oil, shea oil, sal oil, coconut oil, japan wax, jojoba oil, grape seed oil and avocado oil; animal fats and oils such as mink oil, egg yolk oil, beef tallow, milk fat and lard; waxes such as bees wax, spermaceti, lanolin, carnauba wax and candelilla wax; hydrocarbons such as liquid paraffin, squalene, squalane, microcrystalline wax, ceresin wax, paraffin wax and vaseline; natural and synthetic fatty acids such as lauric acid, myristic acid, stearic acid, oleic acid, isostearic acid and behenic acid; natural and synthetic higher alcohols such as cetanol, stearyl alcohol, hexyldecanol, octyldecanol and lauryl alcohol; esters such as isopropyl myristate, isopropyl palmitate, octyldodecyl myristate, octyldodecyl oleate and cholesterol oleate and ethers; silicone oil; and the like. These fats and oils may be used singly or in any combination of two or more.

When these fats and oils are used, the ratio in the external composition of the present invention is not particularly limited as far as it does not affect the skin and mucous membranes and does not impair the effect of the present invention, it can be suitably selected and used in a range such that it is contained in a ratio of 0.01 to 70 w/w % in the external composition of the present invention, and from the viewpoint of stability of the active ingredient in the external composition of the present invention, impression from use on the skin and the like, it is used in a range of preferably 0.1 to 60 w/w %, and more preferably 0.1 to 50 w/w %. Also, the ratio of the fats and oils based on 1 part by weight of the total content of the component (A) contained in the external composition of the present invention is in a range of 0.0001 to 10 parts by weight, preferably from 0.0001 to 8 parts by weight, and more preferably from 0.0005 to 5 parts by weight. Furthermore, from the viewpoint of improving stability of ascorbic acid, the ratio of the fats and oils based on 1 part by weight of the total content of the component (A) is in a range of 0.001 to 10 parts by weight, preferably 0.001 to 5 parts by weight, and more preferably 0.001 to 1 part by weight.

Saccharides are not particularly limited as long as they are used as components of external preparations in the field of pharmaceuticals, quasi-drugs or cosmetics. Examples of saccharides include monosaccharides (for example, glucose, galactose, mannose, ribose, arabinose, xylose, deoxyribose, fructose, ribulose, lyxose, and the like), disaccharides (for example, sucrose, trehalose, lactose, maltose, cellobiose, and the like), oligosaccharides (for example, lactulose, raffinose, pullulan, and the like), cellulose or derivatives thereof (for example, methylcellulose, ethylcellulose, hydroxyethylcellulose, hydroxypropylcellulose, carboxymethylcellulose, carboxyethylcellulose, nitrocellulose, and the like), polysaccharides [for example, chondroitin sulfuric acid, hyaluronic acid, dermatan, heparan, heparin, keratan or salts thereof (for example, pharmaceutically or physiologically acceptable salts such as sodium chondroitin sulfate, sodium hyaluronate, dermatan sulfate, heparan sulfate and keratan sulfate, and like), and like], and sugar alcohols (for example, mannitol, xylitol, erythritol, pentaerythritol, maltitol, sorbitol, polydextrose, and the like), and besides, xylose, inositol, dextrin and derivatives thereof, honey, black sugar extract, and the like. These saccharides may be used singly or in any combination of two or more.

To the external composition of the present invention, various components that are generally used as components of external preparations in the field of pharmaceuticals, quasi drugs, or cosmetics, such as amino acids, irritation reducing agents, thickeners, preservatives, ultraviolet protective agents, coloring agents, dispersants, pH adjusters, perfumes and the like, can be contained as required, in the quantitative and qualitative ranges that do not impair qualities such as appearance stability and viscosity and do not impair the effect of the present invention. These components can be contained singly or in any combination of two or more.

The external composition of the present invention can be prepared into various desired forms such as paste, mousse, gel, liquid, emulsion, cream, sheet (carrying the substrate), aerosol, spray or the like, by blending and mixing (A) at least one member selected from the group consisting of ascorbic acid and salts of ascorbic acid, (B) at least one member selected from the group consisting of 3-O-ethylascorbic acid, salts of 3-O-ethylascorbic acid, and hydroxylated lecithin, and (C) polyethylene glycol, and the above arbitrary components as necessary, and further, blending other solvents, a usually used base of external preparations or the like as necessary. These can be produced by conventional methods in the art.

It is particularly preferable that the external composition of the present invention is a transparent or translucent composition obtained by solubilizing ascorbic acid and/or salts thereof. Here, "solubilizing" is defined as follows. That is, for example, it refers to those with a transmittance in a range of 80 to 100%, preferably 85 to 100%, and more preferably 90 to 100%, as a transmittance at a wavelength of 700 nm using a spectrophotometer or photoelectric photometer UV-2450 (manufactured by SHIMADZU CORPORATION) by ultraviolet-visible spectrophotometry. The transmittance of water is defined as 100%. The solubilized composition of the present invention has a transparent or translucent appearance. More specifically, the permeability measurement method is in accordance with the method described in The Japanese Pharmacopoeia, 16th Edition, [B] General Tests, 2. Physical Methods, Spectroscopic Methods, 2.24 Ultraviolet-visible Spectrophotometry.

The external composition of the present invention is not limited, but is preferably in the form of a liquid containing water in a ratio of 0.01 w/w % to 60 w/w %, more preferably in the form of a liquid containing water in a ratio of 0.01 w/w % to 50 w/w %, and particularly preferably in the form of a liquid containing water in a ratio of 0.1 w/w % to 40 w/w %.

In one embodiment of the present invention, it is possible to suppress precipitation of ascorbic acid or a salt thereof even in a composition containing a small amount of water, as described above. Furthermore, it is possible to suppress decomposition of ascorbic acid.

[Viscosity]

The external composition of the present invention can be prepared as a composition having an appropriate viscosity desired for use of an external composition particularly for application to the skin. Although the viscosity of the external composition of the present invention is not particularly limited, for example, the viscosity when measured at 25° C. using an E type viscometer is usually about 1 to 300 mPa·s, preferably about 1 to 200 mPa·s, more preferably about 1 to 100 mPa·s, and most preferably about 1 to 50 mPa·s. More specifically, the viscosity measurement method is in accordance with the method described in The Japanese Pharmacopoeia, 16th Edition, [B] General Tests, 2. Physical Methods, Other Physical Methods, 2.53 Viscosity Determination, 2. Method II Viscosity measurement by rotational viscometer, 2.1.3. Cone-flat plate-type rotational viscometer (Cone-plate type viscometer).

[pH]

The external composition of the present invention usually has an acidity or alkalinity of pH 1 to 8, and desirably has an acidic range of preferably pH 2 to 7, and more preferably pH 2 to 6, from the viewpoint of stability of ascorbic acid, low irritation to the skin and mucous membranes, and good impression from use on the skin.

[Use]

The external composition of the present invention is particularly effective as a skin-whitening agent, an anti-inflammatory agent, and an anti-aging agent. For example, it has effects of acne prevention and treatment, and anti-oxidation. In addition, by application to the skin, transparency of the skin increases, moisture is retained, texture is adjusted, and the effect of suppressing roughness is exerted in some cases. Furthermore, the effects of making the pores inconspicuous and conditioning and moisturizing the skin and the like are exerted in some cases, and it can also be used for prevention and treatment of spots.

The external composition of the present invention can be used as various external compositions belonging to the field of cosmetics, external pharmaceuticals or quasi-external drugs, such as basic cosmetics such as essence, skin lotion, sunscreen cream, milky lotion, cream, lotion, oil and pack; make-up cosmetics such as foundation, lipstick, lip cream, mascara, eyeshadow, eyeliner, eyebrows and beauty nails; washing agents such as face washings, cleansing and body cleansing agents; antiperspirant agents, athlete's foot treatment agents, antipruritic agents, wound healing agents, debriding agents, detergents, anti-inflammatory analgesics, acne therapeutic agents, hemorrhoids, disinfectants, skin-whitening agents, and ultraviolet protective agents. From the action effect on the skin, the present invention is preferably used for products applied to external skin such as skin external preparation (preparation for external skin).

[Stabilization Method]

The present invention also encompasses a method for stabilizing (A) at least one member selected from the group consisting of ascorbic acid and salts of ascorbic acid. In the present invention, the method for stabilizing an ascorbic acid can achieve a preparation containing an ascorbic acid at a high concentration (for example, 20% or more, 25% or more, or the like), by a combined use of (A) at least one member selected from the group consisting of ascorbic acid and salts of ascorbic acid, (B) at least one member selected from the group consisting of 3-O-ethylascorbic acid, salts of 3-O-ethylascorbic acid, and hydroxylated lecithin, and (C) polyethylene glycol. That is, the present invention relates to a method for imparting stability to an external composition containing (A) at least one member selected from the group consisting of ascorbic acid and salts of ascorbic acid, by a combined use of (A) at least one member selected from the group consisting of ascorbic acid and salts of ascorbic acid, (B) at least one member selected from the group consisting of 3-O-ethylascorbic acid, salts of 3-O-ethylascorbic acid, and hydroxylated lecithin, and (C) polyethylene glycol. Here, the stabilization is not limited, and it refers that stability is secured, for example, even under high temperature or low temperature. Specifically, it refers that precipitation of ascorbic acid or a salt thereof is not suppressed even when at least the external composition is stored at 4° C. for 1 week, the residual ratio of ascorbic acid is 85% or more even when stored at 50° C. for 2 weeks, or the like.

In the method of the present invention, (A) at least one member selected from the group consisting of ascorbic acid and salts of ascorbic acid, (B) at least one member selected from the group consisting of 3-O-ethylascorbic acid, salts of 3-O-ethylascorbic acid, and hydroxylated lecithin, and (C) polyethylene glycol and contents thereof are the same as those used in the external composition. Furthermore, the product obtained by this method can be used in known or commonly used dosage and dose divided into one to several times per day depending on the use and the like.

EXAMPLES

Examples 1 to 36, Comparative Examples 1 to 25

Next, the present invention will be specifically described with reference to examples, but the present invention is not limited to the following examples. The unit of the amount of each component in the tables is w/w %.

External compositions (Examples 1 to 36, Comparative Examples 1 to 25) having the compositions shown in Tables 1 to 12 were prepared according to a conventional method. The external compositions having the compositions shown in Tables 1 to 12 contain (A) at least one member selected from the group consisting of ascorbic acid and salts of ascorbic acid, (B) at least one member selected from the group consisting of 3-O-ethylascorbic acid, and salts of 3-O-ethylascorbic acid, and (C) polyethylene glycol.

[Confirmation Test for Ascorbic Acid Precipitation Suppression]

Evaluation of the presence or absence of precipitation of ascorbic acid when a preparation was stored at low temperature was visually observed. Specifically, ascorbic acid was added to a mixed solution of various components according to the prescription (w/w %) described in the prescription table, and dissolved by mixing and heating the mixture at 60° C. for 10 minutes to prepare a preparation. The prepared preparation was filled in a transparent glass bottle, and the glass bottle was allowed to stand at 4° C. under light-shielding conditions and stored for 1 week or 8 weeks, then each test solution was visually observed to determine the presence or absence of crystal precipitation.

<Evaluation Criteria>

○: Conditions in which precipitates cannot be visually confirmed x: Conditions in which precipitates can be visually confirmed

[Ascorbic Acid Stability Test]

The preparations of Examples and Comparative Examples 1 and 2 were left at 50° C. for 2 weeks, and the residual ratio (%) of ascorbic acid was measured by HPLC. The content of ascorbic acid in a solution sample was determined by dispensing 2.0 g from the solution sample, diluting this with purified water and a mercaptoethanol aqueous solution (1000:1), and applying this as a measurement sample on HPLC manufactured by Agilent (mobile phase: acetonitrile/0.02 M phosphate solution (pH 3.0) (1:9), detection wavelength of absorbance: 270 nm) equipped with a reverse phase column (CAPCELL PAK C18 SG120, manufactured by Shiseido Co., Ltd.) and measuring the amount of L-ascorbic acid contained in the solution.

For the measurement, dehydroascorbic acid was converted to L-ascorbic acid by placing the sample solution in the presence of mercaptoethanol as a reducing agent, and the total amount of both was measured as the amount of L-ascorbic acid. When the ascorbic acid content in the solution sample stored at 4° C. for 2 weeks is defined as 100, the ascorbic acid residual ratio (%) is expressed as a ratio of ascorbic acid content in the solution sample after storage at 50° C. for 2 weeks (Formula 1).

Ascorbic acid residual ratio (%)=Quantitative ascorbic acid value in 50° C.·2 W storage sample/ Quantitative ascorbic acid value in 4° C.·2 W storage sample×100     Formula (1)

The results of formulation in which ascorbic acid, 3-O-ethylascorbic acid and polyethylene glycol (hereinafter also referred to as PEG) are mixed are shown in Tables 1 and 2. W in the tables represents week(s). For example, 1 W is 1 week, and 8 W is 8 weeks.

TABLE 1

| Component name | Example 1 | Example 2 | Example 3 | Example 4 |
| --- | --- | --- | --- | --- |
| Ascorbic acid | 20 | 20 | 20 | 20 |
| 3-O-Ethylascorbic acid | 0.5 | 0.5 | 0.5 | 0.5 |
| Purified water | 20 | 20 | 20 | 20 |
| PEG200 | 59.5 | — | — | — |
| PEG300 | — | 59.5 | — | — |

TABLE 1-continued

| Component name | Example 1 | Example 2 | Example 3 | Example 4 |
|---|---|---|---|---|
| PEG400 | — | — | 59.5 | — |
| PEG600 | — | — | — | 59.5 |
| Total | 100 | 100 | 100 | 100 |
| Solubility immediately after preparation | ○ | ○ | ○ | ○ |
| 4° C. 1 W (Ascorbic acid precipitation) | ○ | ○ | ○ | ○ |
| 4° C. 8 W (Ascorbic acid precipitation) | ○ | ○ | ○ | ○ |
| Ascorbic acid residual ratio | 98 | 99 | 97 | 98 |

TABLE 2

| Component name | Example 5 | Example 6 | Example 7 |
|---|---|---|---|
| Ascorbic acid | 25 | 25 | 25 |
| 3-O-Ethylascorbic acid | 0.5 | 0.5 | 0.5 |
| Purified water | 20 | 20 | 20 |
| PEG200 | 54.5 | — | — |
| PEG300 | — | 54.5 | — |
| PEG400 | — | — | 54.5 |
| Total | 100 | 100 | 100 |
| Solubility immediately after preparation | ○ | ○ | ○ |
| 4° C. 1 W (Ascorbic acid precipitation) | ○ | ○ | ○ |

It can be seen that ascorbic acid can be stably blended by combining ascorbic acid, 3-O-ethylascorbic acid and PEG. Furthermore, it can be seen that the residual ratio of ascorbic acid is also high.

TABLE 3

| Component name | Example 8 | Example 9 | Example 10 | Example 11 | Example 12 | Example 13 | Example 14 | Example 15 |
|---|---|---|---|---|---|---|---|---|
| Ascorbic acid | 20 | 25 | 20 | 25 | 20 | 25 | 20 | 25 |
| Trimethylglycine | 5 | 5 | 5 | 5 | 5 | 5 | 5 | 5 |
| 3-O-Ethylascorbic acid | 0.5 | 0.5 | 0.5 | 0.5 | 0.5 | 0.5 | 0.5 | 0.5 |
| Purified water | 20 | 20 | 20 | 20 | 20 | 20 | 20 | 20 |
| PEG200 | 54.5 | 49.5 | — | — | — | — | — | — |
| PEG300 | — | — | 54.5 | 49.5 | — | — | — | — |
| PEG400 | — | — | — | — | 54.5 | 49.5 | — | — |
| PEG600 | — | — | — | — | — | — | 54.5 | 49.5 |
| Total | 100 | 100 | 100 | 100 | 100 | 100 | 100 | 100 |
| Solubility immediately after preparation | ○ | ○ | ○ | ○ | ○ | ○ | ○ | ○ |
| 4° C. 1 W (Ascorbic acid precipitation) | ○ | ○ | ○ | ○ | ○ | ○ | ○ | ○ |
| 4° C. 8 W (Ascorbic acid precipitation) | ○ | ○ | ○ | ○ | ○ | ○ | ○ | ○ |
| Ascorbic acid residual ratio | 100 | 95 | 98 | 95 | 98 | 95 | 97 | 87 |

TABLE 4

| Component name | Example 16 | Example 17 | Example 18 | Example 19 | Example 20 | Example 21 | Example 22 | Example 23 |
|---|---|---|---|---|---|---|---|---|
| Ascorbic acid | 20 | 25 | 20 | 25 | 20 | 25 | 20 | 25 |
| Trimethylglycine | 5 | 5 | 5 | 5 | 5 | 5 | 5 | 5 |
| Diethylene glycol monoethyl ether | 30 | 30 | 30 | 30 | 30 | 30 | 30 | 30 |
| 3-O-Ethylascorbic acid | 0.5 | 0.5 | 0.5 | 0.5 | 0.5 | 0.5 | 0.5 | 0.5 |
| Purified water | 20 | 20 | 20 | 20 | 20 | 20 | 20 | 20 |
| PEG200 | 24.5 | 19.5 | — | — | — | — | — | — |
| PEG300 | — | — | 24.5 | 19.5 | — | — | — | — |
| PEG400 | — | — | — | — | 24.5 | 19.5 | — | — |
| PEG600 | — | — | — | — | — | — | 24.5 | 19.5 |
| Total | 100 | 100 | 100 | 100 | 100 | 100 | 100 | 100 |
| Solubility immediately after preparation | ○ | ○ | ○ | ○ | ○ | ○ | ○ | ○ |

TABLE 4-continued

| Component name | Example 16 | Example 17 | Example 18 | Example 19 | Example 20 | Example 21 | Example 22 | Example 23 |
|---|---|---|---|---|---|---|---|---|
| 4° C. 1 W (Ascorbic acid precipitation) | ○ | ○ | ○ | ○ | ○ | ○ | ○ | ○ |
| 4° C. 8 W (Ascorbic acid precipitation) | ○ | ○ | ○ | ○ | ○ | ○ | ○ | ○ |
| Ascorbic acid residual ratio | 94 | 97 | 92 | 92 | 96 | 97 | — | 99 |

As shown in Tables 3 and 4, it can be seen that, in the case of formulation in which ascorbic acid, 3-O-ethylascorbic acid, PEG, and trimethylglycine are mixed, precipitation is not detected at 4° C. 8 W even in 25% ascorbic acid preparation. It was shown that, by combining ascorbic acid, 3-O-ethylascorbic acid, PEG and trimethylglycine, ascorbic acid can be further more stably blended at high concentration even when it is left, for example, at 4° C. for 8 weeks.

The transmittance at a measurement wavelength of 700 nm of the compositions shown in the examples was all between 90% and 100%.

In addition, in an ascorbic acid-containing composition in which a mixed solvent of various types of PEG and water and ascorbic acid and 3-O-ethylascorbic acid are mixed did not decompose L-ascorbic acid even when stored under a high temperature state, and the examples showed excellent stability over a long period of time. Specifically, regarding the compositions containing 20% and 25% ascorbic acid, it showed high stability as compared with Comparative Examples 1 and 2 described later, which consisted only of ascorbic acid and water. As a result, it can be seen that ascorbic acid is stably retained in an aqueous medium containing PEG.

Furthermore, a formulation in which high concentration of ascorbic acid, 3-O-ethylascorbic acid, PEG, and trimethylglycine were blended was prepared.

TABLE 5

| Component name | Example 24 | Example 25 | Example 26 | Example 27 |
|---|---|---|---|---|
| Ascorbic acid | 30 | 30 | 30 | 30 |
| Trimethylglycine | 5 | 5 | 5 | 5 |
| 3-O-Ethylascorbic acid | 1 | 1 | 1 | 1 |
| Purified water | 20 | 20 | 20 | 20 |
| Diethylene glycol monoethyl ether | 10 | 10 | — | — |
| 1,3-PG | — | 10 | — | 10 |
| PEG200 | 34 | 24 | 44 | 34 |
| Total | 100 | 100 | 100 | 100 |
| Solubility immediately after preparation | ○ | ○ | ○ | ○ |
| 4° C. · 1 W (Ascorbic acid precipitation) | ○ | ○ | ○ | ○ |
| 4° C. · 8 W (Ascorbic acid precipitation) | ○ | ○ | ○ | ○ |

As a result, even with a 30% ascorbic acid preparation, it was shown that, by combining ascorbic acid, 3-O-ethylascorbic acid, PEG and trimethylglycine, ascorbic acid can be stably blended at high concentration even when it is left, for example, at 4° C. for 8 weeks. The transmittance at a measurement wavelength of 700 nm of the compositions shown in the examples of Table 5 was all between 90% and 100%.

On the other hand, even in a formulation containing ascorbic acid at a relatively low concentration, problems such as precipitation of ascorbic acid and the like were not found. For example, the results of preparing formulations containing 3% to 10% ascorbic acid, 3-O-ethylascorbic acid, and PEG and examining the formulations were shown in Table 6.

TABLE 6

| Component name | Example 28 | Example 29 | Example 30 |
|---|---|---|---|
| Ascorbic acid | 3 | 5 | 10 |
| 3-O-Ethylascorbic acid | 0.1 | 0.1 | 0.1 |
| Purified water | 1 | 1 | 1 |
| PEG200 | 95.9 | 93.9 | 88.9 |
| Total | 100 | 100 | 100 |
| Solubility immediately after preparation | ○ | ○ | ○ |
| 4° C. · 1 W (Ascorbic acid precipitation) | ○ | ○ | ○ |
| 4° C. · 8 W (Ascorbic acid precipitation) | ○ | ○ | ○ |
| Ascorbic acid residual ratio | 96 | 98 | 99 |

Thus, it can be confirmed that 3% to 10% ascorbic acid preparation has no precipitation of ascorbic acid at 4° C. for 2 weeks, in formulations containing ascorbic acid, 3-O-ethylascorbic acid, and PEG. The transmittance at a measurement wavelength of 700 nm of the compositions shown in the examples of Table 6 was all between 90% and 100%. In addition, L-ascorbic acid was not decomposed even when stored under a high temperature state, and the examples showed excellent stability over a long period of time. Specifically, regarding the compositions containing 3%, 5%, and 10% ascorbic acid, it showed high stability as compared with Comparative Examples 23 to 25 consisted only of ascorbic acid and water.

In addition, precipitation of ascorbic acid was not found even in a formulation containing a relatively low concentration of PEG. For example, the results of preparing formulations containing ascorbic acid, 3-O-ethylascorbic acid, and 1 to 10% PEG and examining the formulations were shown in Table 7.

TABLE 7

| Component name | Example 31 | Example 32 | Example 33 | Example 34 | Example 35 | Example 36 |
|---|---|---|---|---|---|---|
| Ascorbic acid | 25 | 25 | 25 | 25 | 25 | 25 |
| Trimethylglycine | 5 | 5 | 5 | 5 | 5 | 5 |

TABLE 7-continued

| Component name | Example 31 | Example 32 | Example 33 | Example 34 | Example 35 | Example 36 |
|---|---|---|---|---|---|---|
| Diethylene glycol monoethyl ether | 48.5 | 44.5 | 39.5 | 48 | 44 | 39 |
| 3-O-Ethylascorbic acid | 0.5 | 0.5 | 0.5 | 1 | 1 | 1 |
| Purified water | 20 | 20 | 20 | 20 | 20 | 20 |
| PEG400 | 1 | 5 | 10 | 1 | 5 | 10 |
| Total | 100 | 100 | 100 | 100 | 100 | 100 |
| Solubility immediately after preparation | ○ | ○ | ○ | ○ | ○ | ○ |
| 4° C. 1 W (Ascorbic acid precipitation) | ○ | ○ | ○ | ○ | ○ | ○ |
| 4° C. 8 W (Ascorbic acid precipitation) | ○ | ○ | ○ | ○ | ○ | ○ |

Thus, it can be confirmed that ascorbic acid is not precipitated at 4° C. for 8 weeks, even in a formulation using relatively high concentration of ascorbic acid and various concentrations of polyethylene glycol. The transmittance at a measurement wavelength of 700 nm of the compositions shown in the examples of Table 7 was all between 90% and 100%.

Next, various comparative examples of the confirmation test for ascorbic acid precipitation suppression are shown in Tables 8 to 11.

TABLE 8

| Component name | Comparative Example 1 | Comparative Example 2 | Comparative Example 3 | Comparative Example 4 | Comparative Example 5 | Comparative Example 6 |
|---|---|---|---|---|---|---|
| Ascorbic acid | 20 | 25 | 20 | 25 | 20 | 25 |
| Diethylene glycol monoethyl ether | — | — | — | — | 60 | 55 |
| 1,3-Butylene glycol | — | — | 60 | 55 | — | — |
| Purified water | 80 | 75 | 20 | 20 | 20 | 20 |
| Total | 100 | 100 | 100 | 100 | 100 | 100 |
| Solubility immediately after preparation | ○ | ○ | ○ | ○ | ○ | ○ |
| 4° C. 1 W (Ascorbic acid precipitation) | ○ | ○ | x | x | x | x |
| 4° C. 8 W (Ascorbic acid precipitation) | ○ | x | x | x | x | x |
| Ascorbic acid residual ratio | 82 | 77 | — | — | — | — |

TABLE 9

| Component name | Comparative Example 7 | Comparative Example 8 | Comparative Example 9 | Comparative Example 10 |
|---|---|---|---|---|
| Ascorbic acid | 20 | 25 | 20 | 25 |
| Diethylene glycol monoethyl ether | — | — | 59.5 | 54.5 |
| Ascorbic acid glucoside | 0.5 | 0.5 | — | — |
| 3-O-Ethylascorbic acid | — | — | 0.5 | 0.5 |
| PEG400 | 59.5 | 54.5 | — | — |
| Purified water | 20 | 20 | 20 | 20 |
| Total | 100 | 100 | 100 | 100 |
| Solubility immediately after preparation | ○ | ○ | ○ | ○ |
| 4° C. 1 W (Ascorbic acid precipitation) | x | x | ○ | x |
| 4° C. 8 W (Ascorbic acid precipitation) | x | x | x | x |

TABLE 10

| Component name | Comparative Example 11 | Comparative Example 12 | Comparative Example 13 | Comparative Example 14 | Comparative Example 15 | Comparative Example 16 | Comparative Example 17 | Comparative Example 18 |
|---|---|---|---|---|---|---|---|---|
| Ascorbic acid | 20 | 25 | 20 | 25 | 20 | 25 | 20 | 25 |
| Purified water | 20 | 20 | 20 | 20 | 20 | 20 | 20 | 20 |
| PEG200 | 60 | 55 | — | — | — | — | — | — |
| PEG300 | — | — | 60 | 55 | — | — | — | — |
| PEG400 | — | — | — | — | 60 | 55 | — | — |
| PEG600 | — | — | — | — | — | — | 60 | 55 |
| Total | 100 | 100 | 100 | 100 | 100 | 100 | 100 | 100 |
| Solubility immediately after preparation | x | x | x | x | ○ | x | ○ | ○ |
| 4° C. 1 W (Ascorbic acid precipitation) | x | x | x | x | x | x | x | x |
| 4° C. 8 W (Ascorbic acid precipitation) | x | x | x | x | x | x | x | x |

TABLE 11

| Component name | Comparative Example 19 | Comparative Example 20 | Comparative Example 21 | Comparative Example 22 |
|---|---|---|---|---|
| Ascorbic acid | 20 | 25 | 20 | 25 |
| 3-O-Ethylascorbic acid | 0.1 | 0.1 | 0.5 | 0.5 |
| 1,3-Butylene glycol | 59.9 | 54.9 | 59.5 | 54.5 |
| Purified water | 20 | 20 | 20 | 20 |
| Total | 100 | 100 | 100 | 100 |
| Solubility immediately after preparation | ○ | ○ | ○ | ○ |
| 4° C. 1 W (Ascorbic acid precipitation) | x | x | x | x |
| 4° C. 8 W (Ascorbic acid precipitation) | x | x | x | x |

TABLE 12

| Component name | Comparative Example 23 | Comparative Example 24 | Comparative Example 25 |
|---|---|---|---|
| Ascorbic acid | 3 | 5 | 10 |
| 3-O-Ethylascorbic acid | — | — | — |
| Purified water | 97 | 95 | 90 |
| PEG200 | — | — | — |
| Total | 100 | 100 | 100 |
| Solubility immediately after preparation | ○ | ○ | ○ |
| Ascorbic acid residual ratio | 82 | 82 | 81 |

From the above results, it can be seen that ascorbic acid is stably retained in an aqueous medium containing PEG. That is, it can be seen that the compositions shown in the examples achieve both properties of precipitation suppression and decomposition suppression of ascorbic acid.

Reference Test Example 1

Ascorbic Acid Transdermal Absorption Test

The transdermal absorbability of the external composition according to some embodiments of the present invention was verified. By improving transdermal absorbability, ascorbic acid permeates into the inside of the skin, so that higher anti-aging effect as a preparation is expected. That is, in some cases, it is possible to exert the effect of ascorbic acid deep into the horny layer.

Transdermal absorbability of ascorbic acid for the external compositions prepared in Examples 17, 19, and 21 was confirmed by measuring ascorbic acid permeated through a reservoir of Franz cell in an infinite closed system.

Specifically, a stirring bar was placed in a Franz cell (PermeGear, Inc., jacketed stationary type-flat jacket-clear-9 mm, 5 mL, permeation area 0.64 square centimeters), and 5 mL of a 0.1% mercaptoethanol aqueous solution was further injected thereinto, then a Strat-M membrane (manufactured by Merck Millipore) was sandwiched between the Franz cell and a ground glass donor and fixed with a clip. To make the infinite closed system, 1 mL each of test samples (external compositions) was placed on a glass donor, and change by evaporation of sample was prevented with aluminum foil.

The thermostatic oven was set at 37° C. and the thermostatic chamber and the Franz cells were connected in series with a silicon tube so that a reservoir solution was kept at a constant temperature. Each Franz cell was set in a stirrer, stirring was started at 400 rpm, and the test was started. After 8 hours from the start of stirring, 200 uL of the reservoir solution was sampled and the ascorbic acid content in the reservoir solution was measured by HPLC. Detection of ascorbic acid by HPLC was performed using a reverse phase column (CAPCELL PAK C18 SG120, manufactured by Shiseido Co., Ltd.) at a wavelength of 270 nm using an ultraviolet absorptiometer, and the content was calculated from a calibration curve.

The results are shown in FIG. 1. As shown in FIG. 1, it was found that transdermal absorbability of the external composition of these examples was very excellent.

Examples 37 to 65, Comparative Examples 26 to 32

External compositions (Examples 37 to 65, Comparative Examples 26 to 32) having the compositions shown in Tables 13 to 19 were prepared according to a conventional method. The unit of the amount of each component in the tables is w/w %. The external compositions having the compositions shown in Tables 13 to 19 contain (A) at least one member selected from the group consisting of ascorbic acid and salts of ascorbic acid, (B-2) hydroxylated lecithin and (C) polyethylene glycol. Furthermore, an external composition containing at least one member selected from the group consisting of 3-O-ethylascorbic acid, and salts of 3-O-ethylascorbic acid as the component (B) was also prepared.

[Confirmation Test for Ascorbic Acid Precipitation Suppression]

In the same manner as in the evaluations of Examples 1 to 36, a confirmation test for ascorbic acid precipitation suppression was performed to determine the presence or absence of crystal precipitation.

The results of the formulation in which ascorbic acid, hydroxylated lecithin (NIKKOL LECINOL SH-50, NIKKOL LECINOL WS-50, manufactured by Nikko Chemicals Co., Ltd.) and polyethylene glycol (hereinafter also referred to as PEG) were blended were shown in Table 13. The meaning of W and the number after polyethylene glycol in the table are the same as those in Tables 1 to 12.

TABLE 13

| Component name | Example 37 | Example 38 | Example 39 | Example 40 | Example 41 | Example 42 | Example 43 | Example 44 |
|---|---|---|---|---|---|---|---|---|
| Ascorbic acid | 3 | 5 | 10 | 20 | 3 | 5 | 10 | 20 |
| NIKKOL LECINOL SH-50 | 0.1 | 0.1 | 0.1 | 0.5 | — | — | — | — |
| NIKKOL LECINOL WS-50 | — | — | — | — | 0.1 | 0.1 | 0.1 | 0.5 |
| Purified water | 1 | 1 | 1 | 20 | 1 | 1 | 1 | 20 |
| PEG200 | 95.9 | 93.9 | 88.9 | 59.5 | 95.9 | 93.9 | 88.9 | 59.5 |
| Total | 100 | 100 | 100 | 100 | 100 | 100 | 100 | 100 |
| Immediately after preparation | ○ | ○ | ○ | ○ | ○ | ○ | ○ | ○ |
| 4° C. · 1 W | ○ | ○ | ○ | ○ | ○ | ○ | ○ | ○ |
| 4° C. · 2 W | ○ | ○ | ○ | ○ | ○ | ○ | ○ | ○ |

It can be seen that ascorbic acid can be stably contained by combining ascorbic acid, hydroxylated lecithin and PEG. Among them, when the composition containing high concentration of ascorbic acid of Example 44 was further experimented up to 8 weeks, it was confirmed that ascorbic acid did not precipitate.

Furthermore, compositions containing higher concentrations of ascorbic acid were prepared.

TABLE 14

| Component name | Example 45 | Example 46 | Example 47 | Example 48 | Example 49 | Example 50 | Example 51 | Example 52 |
|---|---|---|---|---|---|---|---|---|
| Ascorbic acid | 20 | 25 | 20 | 25 | 20 | 25 | 20 | 25 |
| NIKKOL LECINOL WS-50 | 0.5 | 0.5 | 0.5 | 0.5 | — | — | 0.5 | 0.5 |
| NIKKOL LECINOL SH50 | — | — | — | — | 0.5 | 0.5 | — | — |
| Trimethylglycine | 5 | 5 | 5 | 5 | 5 | 5 | 5 | 5 |
| Purified water | 20 | 20 | 20 | 20 | 20 | 20 | 20 | 20 |
| PEG200 | — | — | — | — | 54.5 | 49.5 | 54.5 | 49.5 |
| PEG400 | 54.5 | 49.5 | — | — | — | — | — | — |
| PEG600 | — | — | 54.5 | 49.5 | — | — | — | — |
| Total | 100 | 100 | 100 | 100 | 100 | 100 | 100 | 100 |
| Immediately after preparation | ○ | ○ | ○ | ○ | ○ | ○ | ○ | ○ |
| 4° C. · 1 W | ○ | ○ | ○ | ○ | ○ | ○ | ○ | ○ |
| 4° C. · 2 W | ○ | ○ | ○ | ○ | ○ | ○ | ○ | ○ |
| 4° C. · 8 W | ○ | ○ | ○ | ○ | ○ | ○ | ○ | ○ |

It was shown that, by combining ascorbic acid, hydroxylated lecithin, PEG and trimethylglycine, ascorbic acid can be further more stably contained at high concentration even when it is left, for example, at 4° C. for 8 weeks. The transmittance at a measurement wavelength of 700 nm of the compositions shown in the examples was all between 90% and 100%.

TABLE 15

| Component name | Example 53 | Example 54 | Example 55 | Example 56 |
|---|---|---|---|---|
| Ascorbic acid | 20 | 25 | 20 | 25 |
| NIKKOL LECINOL SH50 | 0.5 | 0.5 | — | — |
| NIKKOL LECINOL WS-50 | — | — | 0.5 | 0.5 |
| Trimethylglycine | 5 | 5 | 5 | 5 |
| Diethylene glycol monoethyl ether | 30 | 30 | 30 | 30 |
| Purified water | 20 | 20 | 20 | 20 |
| PEG200 | 24.5 | 19.5 | 24.5 | 19.5 |
| Total | 100 | 100 | 100 | 100 |
| Immediately after preparation | ○ | ○ | ○ | ○ |
| 4° C. · 1 W | ○ | ○ | ○ | ○ |
| 4° C. · 2 W | ○ | ○ | ○ | ○ |
| 4° C. · 8 W | ○ | ○ | ○ | ○ |

It was shown that, by combining ascorbic acid, hydroxylated lecithin, PEG, trimethylglycine and diethylene glycol monoethyl ether, ascorbic acid can be further more stably contained at high concentration even when it is left, for example, at 4° C. for 8 weeks.

Again, the transmittance at a measurement wavelength of 700 nm of the composition shown in the examples was all between 90% and 100%.

Various comparative examples of the confirmation test for ascorbic acid precipitation suppression are shown in Table 16.

In the table, *LECINOL S-10 means hydrogenated lecithin, a product manufactured by Nikko Chemicals Co., Ltd. **VC glucoside means ascorbic acid glucoside.

From the results of the comparative examples, it can be seen that both components of hydroxylated lecithin and PEG are necessary for precipitation suppression of ascorbic acid. In the case of using hydrogenated lecithin in place of hydroxylated lecithin, preparation of the composition was impossible. Likewise, even when 1,3-butylene glycol was used in the same amount in place of PEG, preparation of the composition was impossible. It was confirmed that the transmittance was less than 85% in the measurement immediately after production, in any of the comparative examples that could be prepared.

Next, a composition containing 3-O-ethylascorbic acid in addition to ascorbic acid, hydroxylated lecithin and PEG was prepared as an additional component, and a similar storage test was performed. The results are shown in Tables 17 to 19.

TABLE 17

| Component name | Example 57 | Example 58 |
|---|---|---|
| Ascorbic acid | 20 | 20 |
| NIKKOL LECINOL SH50 | 0.5 | — |
| NIKKOL LECINOL WS-50 | — | 0.5 |
| 3-O-Ethylascorbic acid | 0.5 | 0.5 |
| Purified water | 20 | 20 |
| PEG200 | 59 | 59 |
| Total | 100 | 100 |
| Immediately after preparation | ○ | ○ |
| 4° C. · 1 W | ○ | ○ |
| 4° C. · 2 W | ○ | ○ |
| 4° C. · 8 W | ○ | ○ |

[0150]
It was shown that 20% ascorbic acid can be stably contained in the compositions containing ascorbic acid, hydroxylated lecithin, PEG and 3-O-ethylascorbic acid even when these are left, for example, at 4° C. for 8 weeks. The

TABLE 16

| Component name | Comparative Example 26 | Comparative Example 27 | Comparative Example 28 | Comparative Example 29 | Comparative Example 30 | Comparative Example 31 | Comparative Example 32 |
|---|---|---|---|---|---|---|---|
| Ascorbic acid | 10 | 20 | 20 | 20 | 20 | — | — |
| VC Glucoside** | — | — | — | — | — | 20 | 20 |
| Concentrated glycerin | — | 0.5 | — | — | — | — | — |
| NIKKOL LECINOL SH50 | — | — | — | 0.5 | — | 0.5 | — |
| NIKKOL LECINOL WS-50 | — | — | — | — | 0.5 | — | 0.5 |
| NIKKOL LECINOL S-10* | — | — | 0.5 | — | — | — | — |
| 1,3-Butylene glycol | 89 | — | — | 60 | 60 | — | — |
| Purified water | 1 | 20 | 20 | 20 | 20 | 20 | 20 |
| PEG200 | — | 59.5 | 59.5 | — | — | 59.5 | 59.5 |
| Total | 100 | 100 | 100 | 100 | 100 | 100 | 100 |
| Immediately after preparation | x | ○ | Preparation was impossible | Preparation was impossible | Preparation was impossible | Δ | Δ |
| 4° C. · 1 W | x | x | — | — | — | x | x |
| 4° C. · 2 W | x | x | — | — | — | x | x | transmittance at a measurement wavelength of 700 nm of the compositions shown in the examples was all between 90% and 100%.

TABLE 18

| Component name | Example 59 | Example 60 | Example 61 | Example 62 |
|---|---|---|---|---|
| Ascorbic acid | 30 | 30 | 30 | 30 |
| NIKKOL LECINOL WS-50 | 0.5 | 0.5 | 0.5 | 0.5 |
| 3-O-Ethylascorbic acid | 1.0 | 1.0 | 1.0 | 1.0 |
| Trimethylglycine | 5 | 5 | 5 | 5 |
| Diethylene glycol monoethyl ether | 10 | 10 | 10 | — |
| 1,3-Propanediol | — | 10 | 20 | — |
| Purified water | 20 | 20 | 20 | 20 |
| PEG200 | 33.5 | 23.5 | 13.5 | 43.5 |
| Total | 100 | 100 | 100 | 100 |
| Immediately after preparation | ○ | ○ | ○ | ○ |
| 4° C. · 1 W | ○ | ○ | ○ | ○ |
| 4° C. · 2 W | ○ | ○ | ○ | ○ |
| 4° C. · 8 W | ○ | ○ | ○ | ○ |

TABLE 19

| Component name | Example 63 | Example 64 | Example 65 |
|---|---|---|---|
| Ascorbic acid | 25 | 25 | 25 |
| NIKKOL LECINOL WS-50 | 0.5 | 0.5 | 0.5 |
| Trimethylglycine | 5 | 5 | 5 |
| Diethylene glycol monoethyl ether | 48.5 | 44.5 | 39.5 |
| Purified water | 20 | 20 | 20 |
| PEG400 | 1 | 5 | 10 |
| Total | 100 | 100 | 100 |
| Immediately after preparation | ○ | ○ | ○ |
| 4° C. · 1 W | ○ | ○ | ○ |
| 4° C. · 8 W | ○ | ○ | ○ |

It was shown that 25% or 30% ascorbic acid can be stably contained in the compositions containing ascorbic acid, hydroxylated lecithin, PEG and 3-O-ethylascorbic acid even when these are left, for example, at 4° C. for 8 weeks. The transmittance at a measurement wavelength of 700 nm of the compositions shown in the examples was all between 90% and 100%.

Formulation Examples

The formulation examples are shown in Tables 20 to 24 below. Each of the formulation examples is a liquid external composition having a transmittance of 90% to 100% at a measurement wavelength of 700 nm, and can be suitably used for skin lotions, essences, and the like. The contents in the formulation examples are all w/w %.

TABLE 20

| Component name | Formulation Example 1 | Formulation Example 2 | Formulation Example 3 | Formulation Example 4 |
|---|---|---|---|---|
| Ascorbic acid | 3 | 10 | 20 | 25 |
| 3-O-Ethylascorbic acid | 0.1 | 0.2 | 0.5 | 1 |
| PEG200 | — | — | — | 40 |
| PEG300 | — | 20 | — | — |
| PEG400 | — | — | 35 | — |
| PEG600 | 10 | — | — | — |
| Trimethylglycine | 1 | — | 3 | 3 |
| Diethylene glycol monoethyl ether | 15 | 20 | 30 | — |
| 1,3-Propanediol | — | — | — | — |
| Purified water | Appropriate amount | Appropriate amount | Appropriate amount | Appropriate amount |
| Perfume | 0.5 | 0.3 | — | 0.1 |
| Lemon extract | 0.1 | — | — | 0.5 |
| Grapefruit extract | — | 0.5 | — | — |
| Acerola extract | — | — | 0.1 | — |
| Total | 100 | 100 | 100 | 100 |

TABLE 21

| Component name | Formulation Example 5 | Formulation Example 6 | Formulation Example 7 | Formulation Example 8 | Formulation Example 9 |
|---|---|---|---|---|---|
| Ascorbic acid | 25 | 25 | 25 | 30 | 30 |
| 3-O-Ethylascorbic acid | 0.5 | 1 | 1 | 1 | 1 |
| PEG200 | 25 | 10 | 10 | 20 | — |
| PEG300 | — | — | 15 | — | 10 |
| PEG400 | — | 15 | — | — | — |
| PEG600 | — | — | — | 15 | 5 |
| Trimethylglycine | 5 | 10 | 10 | 5 | 5 |
| Diethylene glycol monoethyl ether | 30 | 10 | 10 | — | 35 |
| 1,3-Propanediol | — | — | 5 | 10 | — |
| Purified water | Appropriate amount | Appropriate amount | Appropriate amount | Appropriate amount | Appropriate amount |
| Perfume | 0.3 | 0.1 | 0.4 | 0.1 | 0.5 |
| Lemon extract | — | — | — | 0.1 | — |
| Grapefruit extract | 0.5 | — | — | — | — |
| Acerola extract | — | 0.5 | 0.2 | 0.3 | 0.3 |
| Total | 100 | 100 | 100 | 100 | 100 |

TABLE 22

| Component name | Formulation Example 10 | Formulation Example 11 | Formulation Example 12 | Formulation Example 13 | Formulation Example 14 |
|---|---|---|---|---|---|
| Ascorbic acid | 15 | 20 | 20 | 25 | 25 |
| 3-O-Ethylascorbic acid | 0.1 | 0.5 | 1 | 1 | 2 |
| PEG200 | — | 3 | — | 4 | — |
| PEG300 | — | — | 5 | 4 | 5 |
| PEG400 | 5 | 3 | — | 5 | 5 |
| PEG600 | — | — | 5 | — | 5 |
| PEG1500 | — | 2 | — | — | — |
| Trimethylglycine | 3 | 4 | 5 | 5 | 7 |
| Diethylene glycol monoethyl ether | 45 | 40 | 35 | 25 | 25 |
| 1,3-Propanediol | 5 | — | 3 | 2 | — |
| Dipropylene glycol | 5 | 5 | 3 | 2 | — |
| Purified water | Appropriate amount | Appropriate amount | Appropriate amount | Appropriate amount | Appropriate amount |
| Perfume | 0.3 | 0.3 | 0.4 | 0.5 | 0.5 |
| Lemon extract | — | 0.2 | 0.3 | 0.2 | — |
| Grapefruit extract | 2 | — | 0.2 | 0.2 | — |
| Acerola extract | — | 0.3 | — | 0.1 | 0.5 |
| Total | 100 | 100 | 100 | 100 | 100 |

TABLE 23

| Component name | Formulation Example 15 | Formulation Example 16 | Formulation Example 17 | Formulation Example 18 | Formulation Example 19 | Formulation Example 20 | Formulation Example 21 | Formulation Example 22 | Formulation Example 23 |
|---|---|---|---|---|---|---|---|---|---|
| Ascorbic acid | 3 | 10 | 20 | 25 | 25 | 30 | 30 | 35 | 40 |
| NIKKOL LECINOL WS-50 | 0.1 | 0.2 | 0.5 | 1.0 | — | — | — | — | — |
| NIKKOL LECINOL SH-50 | — | — | — | — | 0.3 | 0.5 | 1 | 1 | 1 |
| PEG200 | — | — | — | 50 | 25 | 10 | 30 | 5 | 1 |
| PEG300 | — | 20 | — | — | — | — | 20 | — | 10 |
| PEG400 | — | — | 35 | — | — | 20 | — | 10 | 10 |
| PEG600 | 10 | — | — | — | — | — | — | 10 | — |
| Trimethylglycine | 1 | — | 3.0 | 5 | — | 5 | 10 | — | 5 |
| Diethylene glycol monoethyl ether | 10 | 20 | 30 | — | — | — | — | — | — |
| 3-O-Ethylascorbic acid | — | — | — | — | — | 0.5 | 1 | — | — |
| Perfume | 0.1 | 0.3 | 0.5 | — | 0.1 | 0.5 | 0.3 | — | — |
| Lemon extract | 0.1 | — | — | 0.3 | — | — | 0.5 | — | — |
| Grapefruit extract | — | 0.01 | — | — | 0.3 | — | — | 0.5 | — |
| Acerola extract | — | — | 0.1 | — | — | 0.3 | — | — | 0.5 |
| Purified water | Appropriate amount | Appropriate amount | Appropriate amount | Appropriate amount | Appropriate amount | Appropriate amount | Appropriate amount | Appropriate amount | Appropriate amount |
| Total | 100 | 100 | 100 | 100 | 100 | 100 | 100 | 100 | 100 |

TABLE 24

| Component name | Formulation Example 24 | Formulation Example 25 | Formulation Example 26 |
|---|---|---|---|
| Ascorbic acid | 30 | 30 | 40 |
| NIKKOL LECINOL WS-50 | — | 1 | — |
| NIKKOL LECINOL SH-50 | — | — | 1 |
| PEG200 | 0.5 | — | — |
| PEG300 | — | — | — |
| PEG400 | — | 1 | — |
| PEG600 | — | — | 3 |
| Trimethylglycine | 1 | 1 | 1 |
| 1,3-Propanediol | 20 | 5 | 5 |
| Diethylene glycol monoethyl ether | 10 | 10 | 20 |
| Polyoxyethylene polyoxypropylene glycol | 0.2 | 0.2 | 0.2 |
| 3-O-Ethylascorbic acid | 1 | — | 1 |
| Perfume | 0.1 | 0.1 | 0.3 |
| Lemon extract | — | 0.1 | — |
| Grapefruit extract | — | — | 0.5 |
| Acerola extract | 0.1 | — | — |
| Purified water | Appropriate amount | Appropriate amount | Appropriate amount |
| Total | 100 | 100 | 100 |

The invention claimed is:

1. A liquid external composition comprising:
(A) at least one member selected from the group consisting of ascorbic acid and salts of ascorbic acid, a concentration of which is 3 w/w % to 40 w/w % based on the weight of the total external composition;
(B) at least one member selected from the group consisting of 3-O-ethylascorbid acid and salts of 3-O-ethylascorbic acid, wherein the ratio of the amount of (B) is 0.0001 to 100 parts by weight based on 1 part weight of the total content of (A); and
(C) polyethylene glycol,
wherein the precipitation of component (A) is suppressed.

2. The liquid external composition according to claim 1, further comprising (D) a low molecular weight betaine.

3. The liquid external composition according to claim 1, further comprising (E) glycol ether.

4. The liquid external composition according to claim 1, further comprising (F) a polyhydric alcohol.

5. The liquid external composition according to claim 1, further comprising hydroxylated lecithin.

6. The liquid external composition according to claim 1, comprising 0.005 w/w % based on the weight of the total external composition or more of at least one member selected from the group consisting of 3-O-ethylascorbic acid and salts of 3-O-ethylascorbic acid.

7. The liquid external composition according to claim 1, comprising 0.01 w/w % based on the weight of the total external composition or more of (C) polyethylene glycol.

8. The liquid external composition according to claim 1, wherein the external composition is a solubilized external composition having a transmittance at a wavelength of 700 nm of 85 to 100%.

9. The liquid external composition according to claim 1, wherein the external composition has a transmittance at a wavelength of 700 nm of 85 to 100% at 4° C.

10. The liquid external composition according to claim 1, wherein the molecular weight of polyethylene glycol is about 150 to 1000.

11. The liquid external composition according to claim 1, wherein the ratio of the amount of polyethylene glycol is 0.001 to 100 parts by weight based on 1 part by weight of the total content of (A).

12. A method for imparting stability to a liquid external composition comprising (A) at least one member selected from the group consisting of ascorbic acid and salts of ascorbic acid, wherein the method comprising the steps of:
combining (A) at least one member selected from the group consisting of ascorbic acid and salts of ascorbic acid, a concentration of which is 3 w/w % to 40 w/w % based on the weight of the total external composition, (B) at least one member selected from the group consisting of 3-O-ethylascorbic acid, salts of 3-O-ethylascorbic acid and (C) polyethylene glycol, wherein the ratio of the amount of (B) is 0.0001 to 100 parts by weight based on 1 part weight of the total content of (A).

* * * * *